(12) United States Patent
Kuroiwa et al.

(10) Patent No.: US 7,330,257 B2
(45) Date of Patent: Feb. 12, 2008

(54) SPECTROSCOPE AND SPECTRUM LASER MICROSCOPE

(75) Inventors: Yoshinori Kuroiwa, Kamagaya (JP); Hisashi Okugawa, Yokosuka (JP)

(73) Assignee: Nikon Corporation, Tokyo (JP)

( * ) Notice: Subject to any disclaimer, the term of this patent is extended or adjusted under 35 U.S.C. 154(b) by 137 days.

(21) Appl. No.: 11/207,872

(22) Filed: Aug. 22, 2005

(65) Prior Publication Data

US 2006/0038996 A1 Feb. 23, 2006

(30) Foreign Application Priority Data

Aug. 23, 2004 (JP) .............................. 2004-242729

(51) Int. Cl.
*G01J 3/28* (2006.01)
(52) U.S. Cl. ...................... 356/326; 356/317; 356/318; 356/328
(58) Field of Classification Search ................ 356/317, 356/318, 328, 226, 326; 250/226
See application file for complete search history.

(56) References Cited

U.S. PATENT DOCUMENTS 5,886,784 A 3/1999 Engelhardt .................. 356/326

2002/0036775 A1* 3/2002 Wolleschensky et al. ... 356/317
2002/0050560 A1* 5/2002 Kabuki et al. .............. 250/226

FOREIGN PATENT DOCUMENTS

| JP | 2001-147159 | 5/2001 |
| JP | 2004-506192 A | 2/2004 |
| WO | WO 02/12864 A1 | 2/2002 |

* cited by examiner

*Primary Examiner*—Gregory J. Toatley, Jr.
*Assistant Examiner*—Abdullahi Nur
(74) *Attorney, Agent, or Firm*—Miles & Stockbridge P.C.

(57) ABSTRACT

An object is to provide a spectroscope and a spectrum laser microscope capable of carrying out sensitivity correction of a multi-channel photodetector with real time. The spectrum laser microscope 100 includes a laser microscope 101 and a spectral analyzer 103 having a multi-channel photodetector 13 composed of a plurality of photodetectors 13*i* for detecting spectral distribution of the light from the laser microscope 101. Sensitivity fluctuation of the plurality of photodetectors 13*i* is calculated from a first luminance data detected before shifting relative position between the spectra and the multi-channel photodetector 13 and a second luminance data detected after shifting. Then, the first luminance data or the second luminance data is corrected.

13 Claims, 4 Drawing Sheets

SPECTROSCOPE AND SPECTRUM LASER MICROSCOPE

The disclosures of the following priority application is herein incorporated by reference:

Japanese Patent Application No. 2004-242729 filed Aug. 23, 2004.

BACKGROUND OF THE INVENTION

1. Field of the Invention

The present invention relates to a spectroscope and a spectrum laser microscope for detecting and analyzing spectra from a sample, in particular, to a spectroscope and a spectrum laser microscope capable of correcting fluctuation in sensitivity of each detector of a multi-channel photodetector.

2. Related Background Art

In the field of biology and medical science, study on intracellular communication is eagerly going on. In this area, a fluorescent microscope is used for exploiting characteristics thereof capable of selectively visualizing functional molecules (such as protein, inorganic substance, and the like) smaller than a cell, and observing interaction between a plurality of functional molecules, in addition to being able to dynamically observe living things alive in an almost natural state (including sufficient moisture in the atmosphere). Among the fluorescent microscopes, a fluorescent confocal laser microscope has recently been getting popular because of being able to obtain a cross-sectional imaging and a high contrast imaging. Fluorescence is emitted from a sample having a specific wavelength range in accordance with various states and conditions such as a kind of a fluorescence agent, a combined state between the fluorescence agent and the sample, and wavelength to be excited. In other words, existence, a state, and reaction of a material in the sample is confirmed from the wavelength of the fluorescence and its quantitative evaluation becomes possible by its intensity.

In order to find out phenomena occurring within a living body by strictly defining substance by analyzing fluorescence into spectra, a laser microscope has recently been proposed, in which the wavelength range of the spectra can be detected at a time by using a multi-channel photodetector constructed by a plurality of photodetectors (which are called as channels). To obtain spectra by this kind of a laser microscope is superior to a fluorescent microscope for detecting a single wavelength such that fluorescence spectrum information of the sample can be obtained visually as a two-dimensional image (for example, see National Stage Patent Application Translated Version Publication No. P2004-506192A).

However, in a laser microscope disclosed in National Stage Patent Application Translated Version Publication No. P2004-506192A, the multi-channel photodetector for detecting spectra (each photodetector (hereinafter called a channel) of anode type PMT (Photo Multiplier Tube) with such as 32 channels) does not have uniform sensitivity (according to quantum efficiency and a multiplication factor) and minute intensity of the spectra of the fluorescence cannot be obtained with required precision upon varying voltage applying to the multi-channel photodetector, so that it is a problem that strictly defining substance is difficult.

SUMMARY OF THE INVENTION

The present invention is made in view of the aforementioned problems and has an object to provide a spectroscope and a spectrum laser microscope capable of carrying out sensitivity correction of a multi-channel photodetector in real time upon detecting fluorescence.

According to a first aspect of the present invention, a spectroscope includes, a spectroscopic device that decomposes light from a microscope into spectra, a multi-channel photodetector that is constructed by a plurality of photodetectors and detects the spectra decomposed by the spectroscopic device all together, a moving means that varies a relative position between the spectra and the multi-channel photodetector along a direction of wavelength dispersion of the spectra, and a calculating means that processes each luminance data from the plurality of photodetectors. The calculating means calculates sensitivity fluctuation of each photodetector of the plurality of detectors from a first luminance data detected before varying the relative position between the spectra and the multi-channel photodetector and a second luminance data detected after varying and corrects the first luminance data or the second luminance data.

In the spectroscope according to the first aspect of the present invention, it is preferable that the second luminance data is detected when the relative position between the spectra and the multi-channel photodetector is varied by the moving means by the amount of one photodetector among the plurality of photodetectors, and wherein the calculating means calculates sensitivity fluctuation of each of the plurality of photodetectors from the first luminance data and the second luminance data detected from a photodetector corresponding to the same wavelength range of the spectra and corrects the first luminance data or the second luminance data.

In the spectroscope according to the first aspect of the present invention, the moving means is preferably arranged on the multi-channel photodetector.

In the spectroscope according to the first aspect of the present invention, the moving means preferably changes an angle of the spectroscopic device relative to the optical axis.

In the spectroscope according to the first aspect of the present invention, it is preferable that the calculating means calculates sensitivity fluctuation of each of the plurality of photodetectors relative to a reference photodetector among the plurality of photodetectors and corrects the first luminance data or the second luminance data.

According to the second aspect of the present invention, a spectroscope includes, a spectroscopic device that decomposes light from a microscope into spectra, a multi-channel photodetector that is constructed by a plurality of photodetectors and detects the spectra decomposed by the spectroscopic device all together, a moving means that varies a relative position between the spectra and the multi-channel photodetector along a direction of wavelength dispersion of the spectra, and a calculating means that processes each luminance data from the plurality of photodetectors. The calculating means calculates sensitivity fluctuation of each photodetector from a first luminance data detected before varying the relative position between the spectra and the multi-channel photodetector and a second luminance data detected after varying and corrects sensitivity fluctuation of each photodetector of the plurality of detectors.

In the spectroscope according to the second aspect of the present invention, the moving means is preferably arranged on the multi-channel photodetector.

In the spectroscope according to the second aspect of the present invention, the moving means preferably changes an angle of the spectroscopic device relative to the optical axis.

According to a third aspect of the present invention, a spectrum laser microscope includes a laser microscope and a spectral analyzer that measures light from the laser microscope. The spectral analyzer includes a spectroscopic device that decomposes the light from the laser microscope into spectra, a multi-channel photodetector that is constructed by a plurality of photodetectors and detects the spectra all together, a moving means that varies a position of the multi-channel photodetector along the direction of wavelength dispersion of the spectra, and a calculating means that processes each luminance data from the plurality of photodetectors. The calculating means calculates sensitivity fluctuation of each photodetector from a first luminance data detected before varying the position of the multi-channel photodetector and a second luminance data detected after shifting and corrects the first luminance data or the second luminance data.

In the spectrum laser microscope according to the third aspect of the present invention, it is preferable that the calculating means corrects the luminance data by optical correction data of the luminance data caused by an optical system of the laser microscope in addition to correcting by the sensitivity correction data caused by sensitivity fluctuation of the multi-channel photodetector.

In the spectrum laser microscope according to the third aspect of the present invention, it is preferable that the optical correction data is a fixed value and the sensitivity correction data is variable.

Other features and advantages according to the invention will be readily understood from the detailed description of the preferred embodiment in conjunction with the accompanying drawings.

BRIEF DESCRIPTION OF THE DRAWINGS

FIGS. 2A and 2B are graphs explaining how to obtain luminance data Ian and Ibn in the spectrum laser microscope according to an embodiment of the present invention, respectively, in which FIG. 2A shows luminance data Ian, and FIG. 2B shows luminance data Ibn.

DESCRIPTION OF THE MOST PREFERRED EMBODIMENTS

An embodiment according to the present invention is explained below with reference to accompanying drawings.

Figure 1:
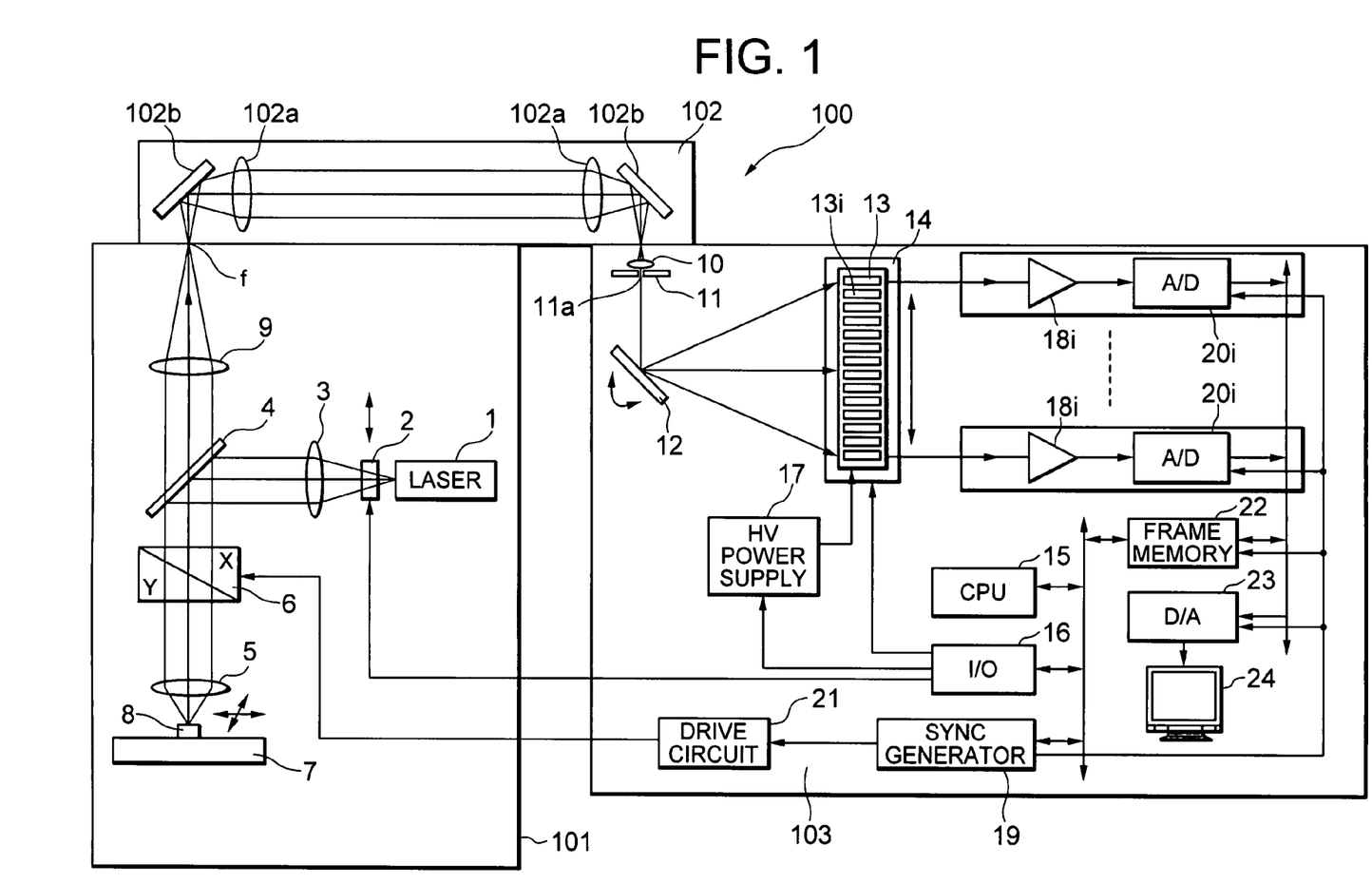
FIG. 1 is a schematic drawing showing a spectrum laser microscope according to an embodiment of the present invention.
Figure 2A:
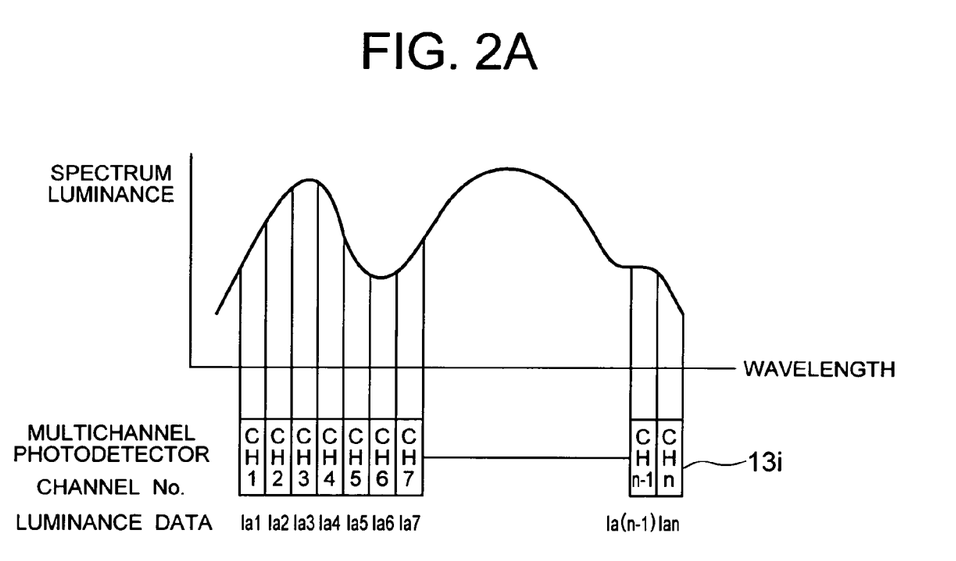
Figure 2B:
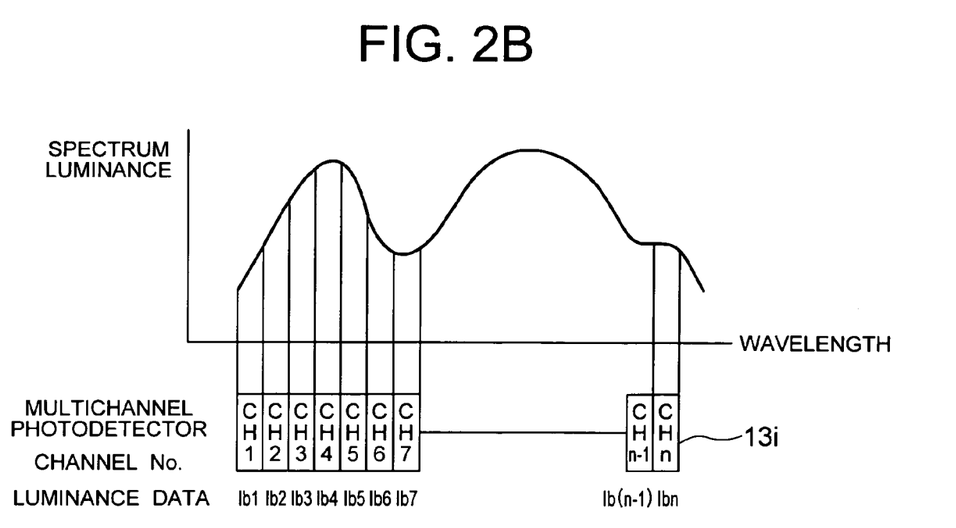
Figure 3:
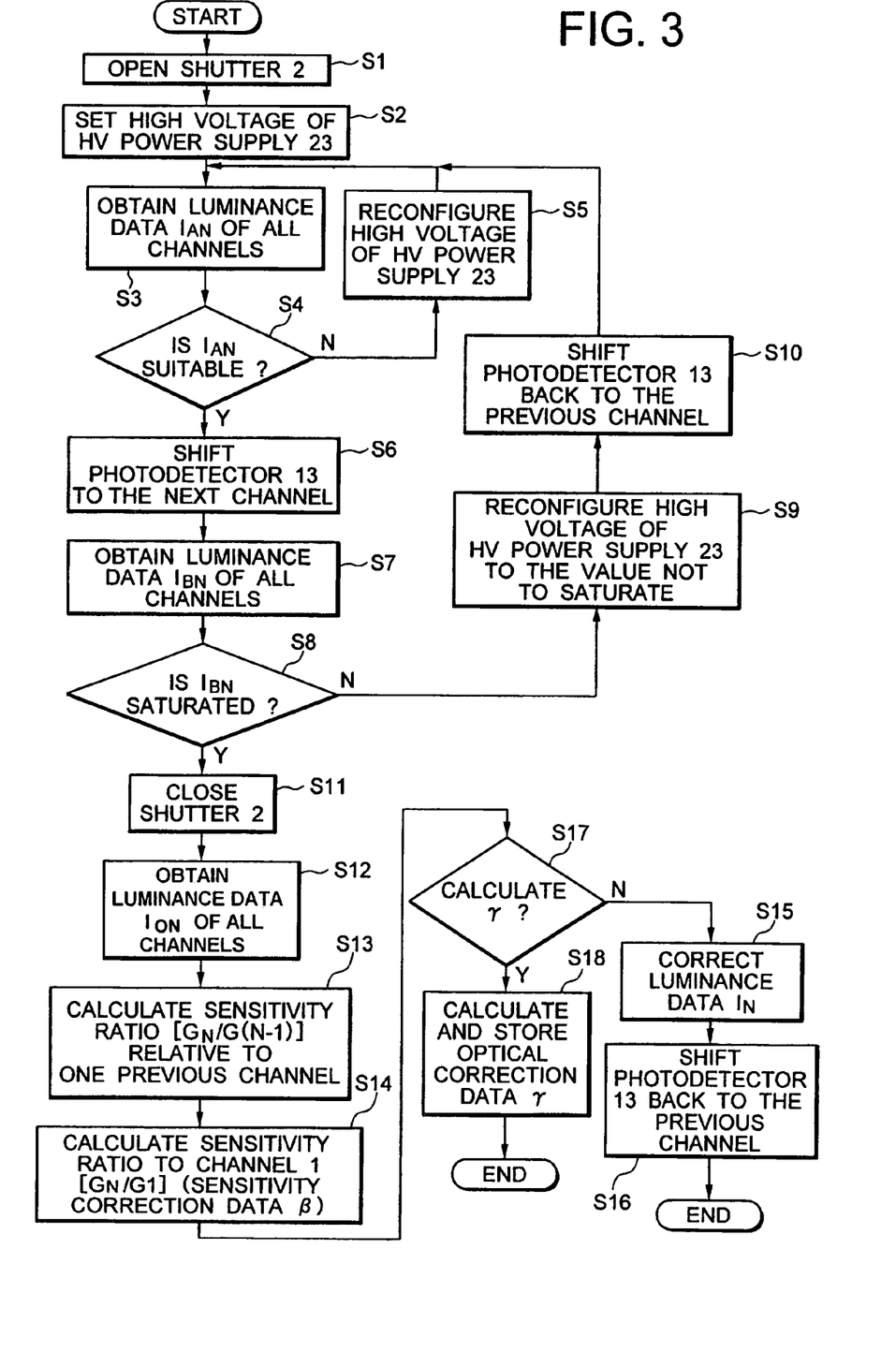
FIG. 3 is a flowchart showing sensitivity correction of the spectrum laser microscope according to an embodiment of the present invention.
Figure 4A:
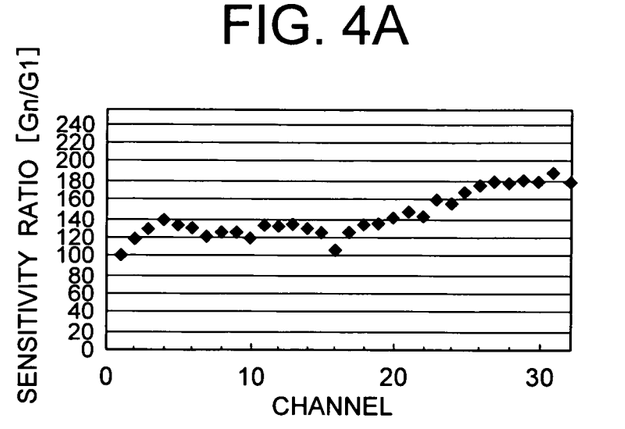
FIGS. 4A, 4B, and 4C are graphs showing an example of sensitivity correction of the spectrum laser microscope according to an embodiment of the present invention.
Figure 4B:
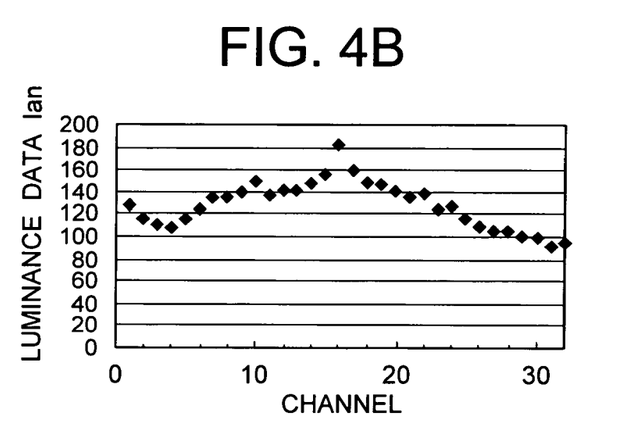
Figure 4C:
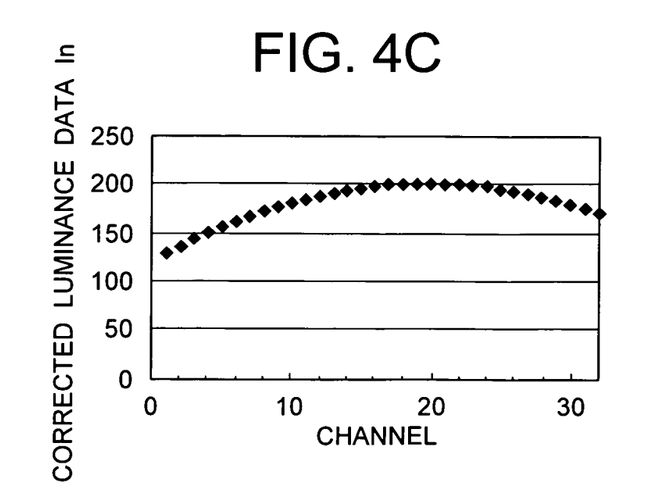

FIG. 1 is a schematic drawing showing a spectrum laser microscope according to an embodiment of the present invention. FIGS. 2A and 2B are graphs explaining how to obtain luminance data Ian and Ibn in the spectrum laser microscope according to an embodiment of the present invention, respectively, in which FIG. 2A shows luminance data Ian, and FIG. 2B shows luminance data Ibn. FIG. 3 is a flowchart showing sensitivity correction of the spectrum laser microscope according to an embodiment of the present invention. FIGS. 4A, 4B, and 4C are graphs showing an example of sensitivity correction of the spectrum laser microscope according to an embodiment of the present invention.

Embodiment

In FIG. 1, the spectrum laser microscope 100 according to an embodiment of the present invention is composed of a laser microscope 101, a relay optical system 102, and a spectrum analyzer (spectroscope) 103.

The laser microscope 101 is composed of a laser light source 1 for emitting excitation light for illuminating a sample (or a reference sample) 8 placed on a stage 7, a collimate lens 3 for substantially collimating the laser light from the laser light source 1, a shutter 2 disposed between the laser light source 1 and the collimate lens 3, a dichroic mirror 4 for reflecting the laser light having a given excitation wavelength from the laser light having substantially collimated laser light come out from the collimate lens 3 in a direction toward an objective lens 5 and transmitting fluorescence produced in the sample 8, a two-dimensional scanner (herein after called an XY scanner) 6 arranged between the dichroic mirror 4 and the objective lens 5 and scans the excitation light two dimensionally in X and Y directions, and a condenser lens 9 that condenses the fluorescence produced by the sample 8 placed on the stage 7 illuminated by the excitation light converged to a point on the sample 8 through the objective lens 5, and condensed by the objective lens 5 to a focal point f through the XY scanner 6 and the dichroic mirror 4.

The relay optical system 102 is composed of optical path deflecting mirrors 102b and 102b for deflecting the fluorescence condensed by the condenser 9, and relay lenses 102a and 102a for relaying condensed fluorescence from the laser microscope 101 to the spectral analyzer 103. By the way, an optical fiber may be used as the relay optical system 102.

The spectral analyzer (spectroscope) 103 is composed of a collimate lens 10 disposed on an optical axis on which fluorescence is incident from the relay optical system 102, a slit 11, a spectroscopic device 12 such as a diffraction grating, a prism, a multi-channel photodetector 13 having a plurality of channels (photodetectors) 13$i$ ($i$=1 through n) for detecting spectra of the fluorescence decomposed by the spectroscopic device 12, a moving means 14 for moving the multi-channel photodetector 13 along the direction of each channel 13$i$, a high voltage power supply 17 for supplying a high voltage to the multi-channel photodetector 13 as instructed by a CPU 15 through an I/O 16, an analog processing circuit 18$i$ ($i$=1 through n) for processing signals from respective channels 13$i$, an A/D converter 20$i$ ($i$=1 through n), a frame memory 22 for storing processed signals, a synchronization signal generator 19 for synchronizing the XY scanner 6 and storing data in the frame memory 22 as instructed by the CPU 15, and a D/A converter 23 for displaying a fluorescence image data stored in the frame memory 22 on a monitor 24.

By the way, variation in relative position between the spectra decomposed by the spectroscopic device 12 and the multi-channel photodetector 13 can be carried out by changing angle of the spectroscopic device 12 relative to the incident light with fixing the multi-channel photodetector 13, or by changing the position of incident light into the spectroscopic device 12.

The shutter 2 is controlled by the CPU 15 through the I/O 16 and the XY scanner 6 is also controlled by the CPU 15 through an XY scanner driver 21. In this manner, the spectrum laser microscope 100 is constructed.

(Initialization of the Spectrum Laser Microscope)

At first, initialization procedure of the whole system of the spectrum laser microscope is explained. Initialization procedure of the whole system of the spectrum laser microscope is carried out by using a reference light whose spectral distribution (wavelength and luminance) is given.

In FIG. 1, a reference sample 8 is placed on the stage 7. Laser light emitted from the laser light source 1 is incident to the dichroic mirror 4 through the collimate lens 3 when the shutter 2 is opened. The laser light incident to the dichroic mirror 4 is reflected by the dichroic mirror 4 in the direction of the objective lens 5, scanned in XY direction by the XY scanner 6 disposed between the dichroic mirror 4 and the objective lens 5, and converged to a point on the reference sample 8 placed on the stage 7 through the objective lens 5. The reference light emitted from the reference sample 8 is condensed by the objective lens 5, moves backward along the optical path, is descanned by the XY scanner 6, and is converged to the focal point f by the condenser lens 9 through the dichroic mirror 4. The converged reference light to the focal point f is incident to the spectral analyzer 103 through the relay optical system 102.

The reference light incident to the spectral analyzer 103 is substantially collimated by the collimate lens 10, shaped by the slit portion 11a of the slit 11 to have a suitable slit width for the spectroscopic device 12, and incident to the spectroscopic device 12. The reference light incident to the spectroscopic device 12 is decomposed by the spectroscopic device 12 to become spectra in the direction of each channel 13i (i=1 through n) of the multi-channel photodetector 13, and incident to each channel 13i of the multi-channel photodetector 13. The incident spectrum is detected with a diffraction width of the spectrum and wavelength resolution $\Delta\lambda$ defined by the pitch of each channel 13i of the multi-channel photodetector 13.

In the multi-channel photodetector 13, in order to detect weak light, an anode-type PMT (HA7260, etc. made by Hamamatsu Photonics K.K.) is used. Each channel 13i (i=1 through 32; hereinafter explained about the case of 32 channels) of the HA7260 is arranged with a separation of 1 mm and the number of channels is 32. Sensitivity of the HA7260 can be varied by applying voltage, so that the CPU 15 controls the high voltage power supply 17 through the I/O 16 to apply high voltage to the multi-channel photodetector 13 in order to obtain a given sensitivity. By the way, in the multi-channel photodetector 13, a separate type solid-state imaging device (such as SPD (Silicon Photo Diode), APD (Avalanche Photo Diode), and the like) may be used in accordance with the intensity of the spectra.

Each channel 13i converts luminance of the incident spectrum into an electric signal. The electric signal is converted into voltage and amplified by the analog processing circuit 18i (i=1 through 32), and converted into digital data by the A/D converter 20i (i=1 through 32) with a sampling clock synchronized with the scanning of the XY scanner 6 controlled by the synchronization signal generator 19. By the way, the XY scanner 6 is driven by the XY scanner driver 21 that receives a synchronization signal from the synchronization signal generator 19. Each channel 13i has the similar analog processing circuit 18i and the A/D converter 20i. With such construction, 32 channels process at a time and luminance data of each channel 13i is stored in the memory of the CPU 15. By the way, it is possible that when the simultaneity of the 32 channels is not necessary, the A/D converter 20i are made to be one and each channel 13i is changed by a multiplexer (not shown) to convert an analog signal into a digital signal.

In this manner, the luminance of each channel 13i corresponding to the spectrum of the reference light from the reference sample 8 is obtained, so that correction data a according to a wavelength of the whole system of the spectrum laser microscope 100 including the optical system and the analyzer can be calculated by the ratio of given luminance data of the reference light to the obtained luminance data. The correction data $\alpha$ includes both of a characteristic (hereinafter denoted as an optical correction data $\gamma$) invariable with time such as characteristic of an optical system of the laser microscope 101 and a characteristic (herein after denoted as sensitivity correction data $\beta$) variable in accordance with using condition (for example, applied voltage, and the like) such as characteristic of the multi-channel photodetector 13, so that $\alpha=\gamma\times\beta$.

Generally, the correction data $\alpha$ ($\alpha=\gamma\times\beta$) is given by an inspection before factory shipment and stored in the spectrum laser microscope 100 (a system composed of a laser microscope 101 and a spectral analyzer 103). Since the correction data $\alpha$ is composed of an optical correction data $\gamma$ invariable with time and a sensitivity correction data $\beta$ variable with time, it is necessary to carry out periodical maintenance, so that it becomes a heavy burden on the user.

In other words, since the sensitivity correction data $\beta$ of a spectral analyzer 103 including a multi-channel photodetector 13 varies (varies with time) in accordance with a using condition and an environment condition, the value of the correction data $\alpha$ varies in response to the variation. Since the variation makes it impossible to correct properly, the user has to ask periodical maintenance for renewing correction data $\alpha$ to the maker, so that it produces inconvenience not to be able to use the system in the meantime.

The embodiment of the present invention provides a system resolving the inconvenience.

As described above, after obtaining the correction data $\alpha$ before factory shipment, the sensitivity correction data $\beta$ of the spectral analyzer 103 is obtained by a method described later, the optical correction data $\gamma$ (the correction data $\gamma$ is a data almost invariant with time) of the laser microscope 101 is calculated from the correction data $\alpha$ and the sensitivity correction data $\beta$. When the calculated optical correction data $\gamma$ is stored in the memory of the CPU 15 in the spectrum laser microscope 100, the luminance data obtained by the spectrum laser microscope 100 can be properly corrected with periodically obtaining by measuring only the sensitivity correction data $\beta$. In other words, the luminance data is come to be corrected by the correction data $\alpha$.

Instead of using the reference sample 8, the similar effect can be obtained such that a removable reference light source is arranged under the stage 7 and the reference light from the reference light source is converged on the focal point of the objective lens 5.

(A Method of Obtaining an Optical Correction Data $\gamma$)

In order to obtain the optical correction data $\gamma$, how to calculate the sensitivity correction data $\beta$ of each channel 13i of the multi-channel photodetector 13 is explained. Although a high sensitivity multi-anode type PMT used as a multi-channel photodetector 13 can change sensitivity by changing high voltage, the sensitivity of each channel varies on this occasion nonuniformly. In particular, when weak fluorescence is to be detected, applying voltage has to be adjusted to become optimum sensitivity relative to the intensity of the incident fluorescence, so that it becomes necessary to obtain the sensitivity correction data of each channel 13*i* upon changing applying voltage. In the spectrum laser microscope 100 according to the embodiment of the present invention, the sensitivity correction data β of each channel 13*i* upon changing applying voltage can be obtained by a method explained below.

Collection of the sensitivity correction data β of each channel 13*i* upon changing applying voltage to the multi-channel photodetector 13 is explained with reference to FIGS. 2 and 3. Up to the step that the reference light is incident to the multi-channel photodetector 13 is the same as described above and duplicated explanation is omitted.

In step S1, the shutter 2 of the laser light source 1 is opened to illuminate the reference sample 8 with the excitation light and the reference light is incident to the spectral analyzer. In step S2, the CPU 15 sets to apply a given voltage to the multi-channel photodetector 13 through the I/O 16. In step S3, the luminance data Ian (n=1 through 32) of all 32 channels are obtained and stored in the memory of the CPU 15. In step S4, whether the level of the obtained luminance data is appropriate or not is checked. In step S5, when the level of the luminance data is not appropriate such that the signal is saturated in the luminance data Ian or the maximum value of the luminance data is too low to use as a luminance data, applying voltage is varied through the high voltage power supply 17. And in steps S3 through S5, the procedure to obtain luminance data Ian is repeated. The relation between the luminance data Ian of each channel 13*i* and the position of the wavelength of the spectra is schematically shown in FIG. 2A. By the way, adjustment of the luminance may be carried out by adjusting the power of the laser light source 1 instead of adjusting the applying voltage of the high voltage power supply 17.

In step S6, the multi-channel photodetector 13 is shifted by one channel (in the direction that the number of the channel on which the light of the same wavelength is incident increases) by means of the moving means 14 (see FIG. 2B). In step S7, in this state, the luminance data Ibn of all 32 channels are obtained again and stored in the memory of the CPU 15. The relation between the luminance data Ibn of each channel 13*i* and the position of the wavelength of the spectra is schematically shown in FIG. 2B. In step S8, when the level of the luminance data is not appropriate such that the signal is saturated in the luminance data Ibn or the maximum value of the luminance data is too low to use as a luminance data, the flow proceeds to step S9. In step S9, applying voltage is varied through the high voltage power supply 17. In step S10, the multi-channel photodetector 13 is shifted back by one channel by means of the moving means 14 and the flow returns to step S3. Then, in steps S3 through S10, the luminance data Ian and Ibn of all 32 channels are obtained again. In step S11, after obtaining desired luminance data Ian and Ibn, the shutter 2 is closed. In step S12, the luminance data Ion of all 32 channels are obtained in the state where no-light is incident to the multi-channel photodetector 13 and stored in the memory of the CPU 15. When the luminance data Ion is negligibly small, the procedure to obtain the luminance data Ion can be omitted.

Then, the sensitivity correction data β of each channel 13*i* is calculated from the luminance data Ian, Ibn and Ion as shown below.

In step S13, the sensitivity ratio [Gn/Gn−1] of each channel 13*i* relative to the previous channel is derived from the following expression:

$$[Gn/Gn-1]=(Ibn-Ion)/(Ia(n-1)-Io(n-1)).$$

As shown in FIGS. 2A and 2B, since the same wavelength range is detected by the channel (n−1) when the luminance data Ian is obtained and by the channel n when the luminance data Ibn is obtained, this shows that the ratio of both sides becomes the sensitivity ratio [Gn/Gn−1] of the channel (n) to the channel (n−1).

In step S14, the sensitivity ratio [Gn/G1] which is the sensitivity correction data β according to the channel one is calculated to each channel from the following expression and stored in the memory of the CPU 15:

$$[Gn/G1]=[G2/G1]\times[G3/G2]\times[G4/G3]\times \ldots \times[Gn/Gn-1]$$

where (n>1).

In step S17, when the procedure is judged as the procedure to calculate the optical correction data γ before shipment, the flow proceeds to step S18. In step S18, the optical correction data γ is calculated (γ=α/β) from the correction data α obtained by using the reference sample 8 and the sensitivity correction data β obtained in step S14 and stored in the memory of the CPU 15.

By the way, in the above-described sensitivity correction, although the correction is carried out by the channel one as a reference channel, the correction can be carried out by the last channel (channel 32) as a reference channel by reversing the shift direction of the multi-channel photodetector 13, or any other channel as a reference channel.

FIGS. 4A through 4C show an example of sensitivity correction. FIG. 4A is a graph showing the sensitivity ratio [Gn/G1] which is the sensitivity correction data β of each channel relative to the channel one obtained by the reference light.

In this manner, even if the voltage applying to the multi-channel photodetector 13 is varied, the spectrum of the light incident to the spectral analyzer 103 is detected as the luminance data Ian and Ibn by the multi-channel photodetector 13 with shifting the position thereof and the sensitivity correction data β can be derived from respective luminance data Ian and Ibn, so that the spectrum can be analyzed with given precision.

Incidentally, although the above-described explanation is for the case using the reference light in order to obtain the optical correction data γ, after obtaining the optical correction data γ, the special reference light is not necessary and the luminance correction can be carried out by using the light from the sample to be measured.

As described above, in the spectrum laser microscope 100, by obtaining the correction data α of the whole spectrum laser microscope 100 and the sensitivity correction data β, which is only variable in accordance with a using condition (such as an applying voltage), of the multi-channel photodetector 13 in advance, the optical correction data γ, in which the spectral distribution is not variable upon using condition, can be calculated, so that even if the using condition is changed, it is sufficient to obtain the sensitivity correction data β of the multi-channel photodetector 13 and it is not necessary to carry out initialization of the whole system of the spectrum laser microscope 100 again by using the reference light having known spectral distribution. Moreover, when the optical system is not changed, the initialization procedure can be omitted by using the above-described correction data α.

By the way, by storing the correction data α in the memory of the CPU 15 or in an external memory, the correction data α can be brought out as need arises. Correction of the spectrum laser microscope 100 can be carried out by using a measured sample instead of a special reference light source and a reference sample.

As described above, after the optical correction data γ has been obtained and stored, it is sufficient to periodically renew only the sensitivity correction data β of the spectral analyzer 103 which is variable with time. Then, the method for obtaining the sensitivity correction data β, properly correcting the luminance data measured by the spectrum laser microscope 100, and analyzing spectrum of the fluorescence from the sample 8 to be measured is explained below.

(Method for Obtaining the Sensitivity Correction Data β from a Sample)

The measurement procedure is the same as described above in the case using a reference sample 8, so the same symbol is used for the explanation.

In FIG. 1, excitation light emitted from the laser light source 1 is scanned by the XY scanner 6, illuminates a sample 8 placed on the stage 7 through the objective lens 5, and produces fluorescence from the sample 8. The fluorescence from the sample 8 is converged by the objective lens 5, reverses the optical path to be descanned by the XY scanner 6, and converged on the focal point f by the condenser lens 9 through the dichroic mirror 4. The converged fluorescence is incident to the spectral analyzer 103 through the relay optical system 102.

The fluorescence incident to the spectral analyzer 103 is substantially collimated by the collimate lens 10, shaped by the slit portion 11a of the slit 11 to have a suitable slit width for the spectroscopic device 12, and incident to the spectroscopic device 12. The fluorescence incident to the spectroscopic device 12 is decomposed by the spectroscopic device 12 to become spectra in the direction of each channel 13i (i=1 through n) of the multi-channel photodetector 13, and incident to each channel 13i of the multi-channel photodetector 13. The incident spectrum is detected with a diffraction width of the spectrum and wavelength resolution Δλ defined by the pitch of each channel 13i of the multi-channel photodetector 13.

After the fluorescence is incident to the multi-channel photodetector 13, the spectral analysis of the fluorescence is carried out in accordance with the flowchart shown in FIG. 3.

In step S1, the fluorescence is incident to the spectral analyzer 103. In step S2, the CPU 15 sets to apply a given voltage to the multi-channel photodetector 13 through the I/O 16. In step S3, the luminance data Ian (n=1 through 32) of all 32 channels are obtained and stored in the memory of the CPU 15. In step S4, whether the level of the obtained luminance data is appropriate or not is checked. In step S5, when the level of the luminance data is not appropriate such that the signal is saturated in the luminance data Ian or the maximum value of the luminance data is too low to use as a luminance data, applying voltage is varied through the high voltage power supply 17. And in steps S3 through S5, the procedure to obtain luminance data Ian is repeated. The relation between the luminance data Ian of each channel 13i and the position of the wavelength of the spectra is schematically shown in FIG. 2A. By the way, adjustment of the luminance may be carried out by adjusting the power of the laser light source 1 instead of adjusting the applying voltage of the high voltage power supply 17.

In step S6, the multi-channel photodetector 13 is shifted by one channel (in the direction that the number of the channel on which the light of the same wavelength is incident increases) by means of the moving means 14 (see FIG. 2B). In step S7, in this state, the luminance data Ibn of all 32 channels are obtained again and stored in the memory of the CPU 15. The relation between the luminance data Ibn of each channel 13i and the position of the wavelength of the spectra is schematically shown in FIG. 2B. In step S8, when the level of the luminance data is not appropriate such that the signal is saturated in the luminance data Ibn or the maximum value of the luminance data is too low to use as a luminance data, the flow proceeds to step S9. In step S9, applying voltage is varied through the high voltage power supply 17. In step S10, the multi-channel photodetector 13 is shifted back by one channel by means of the moving means 14 and the flow returns to step S3. Then, in steps S3 through S10, the luminance data Ian and Ibn of all 32 channels are obtained again. In step S11, after obtaining desired luminance data Ian and Ibn, the shutter 2 is closed. In step S12, the luminance data Ion of all 32 channels are obtained in the state where no-light is incident to the multi-channel photodetector 13 and stored in the memory of the CPU 15. When the luminance data Ion is negligibly small, the procedure to obtain the luminance data Ion can be omitted.

Then, the sensitivity correction data β of each channel 13i is calculated from the luminance data Ian, Ibn and Ion as shown below.

In step S13, the sensitivity ratio [Gn/Gn−1] of each channel 13i relative to the previous channel is derived from the following expression:

$$[Gn/Gn-1]=(Ibn-Ion)/(Ia(n-1)-Io(n-1)).$$

As shown in FIGS. 2A and 2B, since the same wavelength range is detected by the channel (n−1) when the luminance data Ian is obtained and by the channel n when the luminance data Ibn is obtained, this shows that the ratio of both sides becomes the sensitivity ratio [Gn/Gn−1] of the channel (n) to the channel (n−1).

In step S14, the sensitivity ratio [Gn/G1] which is the sensitivity correction data β according to the channel one is calculated to each channel from the following expression and stored in the memory of the CPU 15:

$$[Gn/G1]=[G2/G1]\times[G3/G2]\times[G4/G3]\times \ldots \times[Gn/Gn-1]$$

where (n>1).

In step S15, the luminance data In after correcting the sensitivity correction by the channel one as a reference channel is obtained by the following expression:

$$In=[Gn/G1]\times Ian \text{ (where correction for n=1 is not necessary.)}$$

The luminance data In after correcting sensitivity is that normalized by channel one. In this manner, the sensitivity ratio [Gn/G1] (shown in FIG. 4A) of each channel relative to channel one obtained by the fluorescence and the luminance data Ian shown in FIG. 4B are obtained, and the luminance data Ian is corrected in real time, so that the luminance data In corrected by the sensitivity correction data β is obtained as shown in FIG. 4C. Then, the optical correction data γ is read out from the memory of the CPU 15, the luminance data In is corrected by the optical correction data γ, and the proper luminance data In is obtained.

The luminance data In is stored in the frame memory 22 and displayed on the monitor 24 as an image through the D/A converter 23. By the way, Ibn can be used as the luminance data before correction. In this manner, by processing with the similar normalization to various spectra, comparison of the obtained fluorescence spectra becomes possible.

In step S16, the multi-channel photodetector 13 is shifted back by one channel by means of the moving means 14 and the spectrum measurement is completed.

By the way, in the above-described correction, although the correction is carried out by the channel one as a reference channel, the correction can be carried out by the last channel (channel 32) as a reference channel by reversing the shift direction of the multi-channel photodetector 13, or any other channel as a reference channel.

In this manner, by changing high voltage applying to the multi-channel photodetector 13, the sensitivity of the multi-channel photodetector 13 is set to the optimum sensitivity for the intensity of the incident fluorescence, varying the position of the multi-channel photodetector 13 relative to the spectra of the fluorescence, the sensitivity data Ian and Ibn are obtained, the sensitivity correction data β is calculated by using both of the sensitivity data Ian and Ibn, and the spectral luminance data In after correction can be obtained by using the sensitivity correction data β and the optical correction data γ.

As a variation of the above-described embodiment, after obtaining the sensitivity correction data β, the correction data α of the whole system is calculated by using the optical correction data γ, so that the luminance data In is derived by using the correction data α.

Moreover, when the sensitivity correction data β is calculated, instead of using the sample 8 to be measured, the sensitivity correction data β can be similarly obtained by simply leading a transparent illumination light into the spectral analyzer 103.

In the spectrum laser microscope according to the embodiment of the present invention, since the wavelength characteristics of the whole system including the optical system and the photodetector is corrected in the state of initialization, when the high voltage applying to the multi-channel photodetector is changed in order to measure the fluorescence, the luminance data after correcting the sensitivity can be obtained by the sensitivity correction procedure shown in FIG. 4, so that the fluorescence from the sample can be carried out spectral analysis in real time with given precision.

By the way, the wavelength dependency of the optical system of the spectrum laser microscope 100 has been corrected in the state of the initialization, unless otherwise changing any optical parts, initialization process is not necessary to carry out every time upon measurement.

In the above-described embodiment, the spectral luminance data after correction can be obtained by correcting the obtained luminance data. However, sensitivity of each channel of the multi-channel detector may be made uniform by varying voltage applying to each channel on the basis of the sensitivity correction data of each channel. In this case, after correcting the sensitivity, luminance data is obtained again for obtaining spectral luminance data after correction.

Additional advantages and modification will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A spectroscope comprising:
a spectroscopic device that decomposes light from a microscope into spectra,
a multi-channel photodetector that is constructed by a plurality of photodetectors and detects the spectra decomposed by the spectroscopic device,
a moving means that varies a detecting position of the spectra in the multi-channel photodetector along a direction of wavelength dispersion of the spectra, and
a calculating means that processes each luminance data from the plurality of photodetectors,
wherein the calculating means calculates sensitivity fluctuation of each photodetector of the plurality of detectors from a first luminance data detected before varying the detecting position of the spectra in the multi-channel photodetector and a second luminance data detected after varying and corrects the first luminance data or the second luminance data.

2. The spectroscope according to claim 1, wherein the second luminance data is detected when the detecting position of the spectra in the multi-channel photodetector is varied by the moving means by an amount of one photodetector among the plurality of photodetectors, and wherein the calculating means calculates sensitivity fluctuation of each of the plurality of photodetectors from the first luminance data and the second luminance data detected from a photodetector corresponding to the same wavelength range of the spectra and corrects the first luminance data or the second luminance data.

3. The spectroscope according to claim 1, wherein the moving means is arranged on the multi-channel photodetector.

4. The spectroscope according to claim 3, wherein the second luminance data is detected when the detecting position of the spectra in the multi-channel photodetector is varied by the moving means by an amount of one photodetector among the plurality of photodetectors, and wherein the calculating means calculates sensitivity fluctuation of each of the plurality of photodetectors from the first luminance data and the second luminance data detected from a photodetector corresponding to the same wavelength range of the spectra and corrects the first luminance data or the second luminance data.

5. The spectroscope according to claim 1, wherein the moving means changes an angle of the spectroscopic device relative to the optical axis.

6. The spectroscope according to claim 5, wherein the second luminance data is detected when the detecting position of the spectra in the multi-channel photodetector is varied by the moving means by an amount of one photodetector among the plurality of photodetectors, and wherein the calculating means calculates sensitivity fluctuation of each of the plurality of photodetectors from the first luminance data and the second luminance data detected from a photodetector corresponding to the same wavelength range of the spectra and corrects the first luminance data or the second luminance data.

7. The spectroscope according to claim 2, wherein the calculating means calculates sensitivity fluctuation of each of the plurality of photodetectors relative to a reference photodetector among the plurality of photodetectors and corrects the first luminance data or the second luminance data.

8. A spectroscope comprising:
a spectroscopic device that decomposes light from a microscope into spectra,
a multi-channel photodetector that is constructed by a plurality of photodetectors and detects the spectra decomposed by the spectroscopic device, a moving means that varies a detecting position of the spectra in the multi-channel photodetector along a direction of wavelength dispersion of the spectra, and a calculating means that processes each luminance data from the plurality of photodetectors, wherein the calculating means calculates sensitivity fluctuation of each photodetector from a first luminance data detected before varying the detecting position of the spectra in the multi-channel photodetector and a second luminance data detected after varying and corrects sensitivity fluctuation of each photodetector of the plurality of detectors.

9. The spectroscope according to claim 8, wherein the moving means is arranged on the multi-channel photodetector.

10. The spectroscope according to claim 8, wherein the moving means changes an angle of the spectroscopic device relative to the optical axis.

11. A spectrum laser microscope comprising:

a laser microscope;

a spectroscopic device that decomposes light from the laser microscope into spectra;

a multi-channel photodetector that is constructed by a plurality of photodetectors and detects the spectra;

a moving means that varies a detecting position of the spectra in the multi-channel photodetector along the direction of wavelength dispersion of the spectra; and a calculating means that processes each luminance data from the plurality of photodetectors, wherein the calculating means calculates sensitivity fluctuation of each photodetector from a first luminance data detected before varying the detecting position of the spectra in the multi-channel photodetector and a second luminance data detected after varying and corrects the first luminance data or the second luminance data.

12. The spectrum laser microscope according to claim 11, wherein the calculating means corrects the luminance data by optical correction data of the luminance data caused by an optical system of the laser microscope in addition to correcting by the sensitivity correction data caused by sensitivity fluctuation of the multi-channel photodetector.

13. The spectrum laser microscope according to claim 12, wherein the optical correction data is fixed and the sensitivity correction data is variable.

* * * * *